United States Patent
Baseeth

(10) Patent No.: US 10,240,112 B2
(45) Date of Patent: Mar. 26, 2019

(54) MICROEMULSIONS AND THEIR USE IN METAL WORKING FLUIDS, WOOD STAINS, OR WOOD SEALERS

(71) Applicant: ARCHER DANIELS MIDLAND COMPANY, Decatur, IL (US)

(72) Inventor: Shireen Baseeth, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 30 days.

(21) Appl. No.: 15/316,666

(22) PCT Filed: Jun. 5, 2015

(86) PCT No.: PCT/US2015/034488
§ 371 (c)(1),
(2) Date: Dec. 6, 2016

(87) PCT Pub. No.: WO2015/188103
PCT Pub. Date: Dec. 10, 2015

(65) Prior Publication Data
US 2017/0191008 A1 Jul. 6, 2017

Related U.S. Application Data

(63) Continuation of application No. 62/008,702, filed on Jun. 6, 2014.

(51) Int. Cl.
| | | |
|---|---|---|
| C11D 17/00 | (2006.01) |
| A01N 25/04 | (2006.01) |
| A61K 9/107 | (2006.01) |
| B27K 3/00 | (2006.01) |
| C09K 8/00 | (2006.01) |
| C09D 7/00 | (2018.01) |
| C09D 15/00 | (2006.01) |
| C09K 8/035 | (2006.01) |
| C09K 8/40 | (2006.01) |
| A61L 2/00 | (2006.01) |
| A61L 9/00 | (2006.01) |
| C11D 1/90 | (2006.01) |
| C09D 5/02 | (2006.01) |
| C09D 7/40 | (2018.01) |
| B01F 3/08 | (2006.01) |

(52) U.S. Cl.
CPC .......... *C11D 17/0021* (2013.01); *A01N 25/04* (2013.01); *A61K 9/107* (2013.01); *A61L 2/00* (2013.01); *A61L 9/00* (2013.01); *B27K 3/00* (2013.01); *C09D 5/024* (2013.01); *C09D 7/00* (2013.01); *C09D 7/40* (2018.01); *C09D 15/00* (2013.01); *C09K 8/00* (2013.01); *C09K 8/035* (2013.01); *C09K 8/40* (2013.01); *C11D 1/90* (2013.01); *B01F 2003/0834* (2013.01); *C09K 2208/34* (2013.01)

(58) Field of Classification Search
CPC .......................... C11D 3/0026; C11D 11/0029
See application file for complete search history.

(56) References Cited

U.S. PATENT DOCUMENTS

| | | | |
|---|---|---|---|
| 8,093,293 B2 * | 1/2012 | Seiberg .................... A61K 8/14 514/559 |
| 2003/0166508 A1* | 9/2003 | Zhang ................... A61K 9/1075 424/451 |
| 2004/0247625 A1* | 12/2004 | Carli ...................... A61K 9/113 424/400 |
| 2007/0078057 A1* | 4/2007 | Rowley .................. A01N 25/04 504/206 |
| 2007/0292354 A1* | 12/2007 | Port .................... A61K 49/1812 424/9.321 |
| 2010/0136175 A1* | 6/2010 | Skiff ......................... A23L 2/38 426/72 |
| 2013/0102943 A1* | 4/2013 | Holzdorfer ........... C08F 220/28 602/42 |
| 2015/0139973 A1* | 5/2015 | Steinfeld .............. A61K 9/0048 424/94.4 |
| 2015/0231070 A1* | 8/2015 | Huang ................. A61K 9/1075 424/400 |

* cited by examiner

*Primary Examiner* — Charles I Boyer
(74) *Attorney, Agent, or Firm* — Andrew F. Nilles

(57) ABSTRACT

The present disclosure is directed to compositions including a microemulsion comprising a blend of lecithin, a co-surfactant, and a salt of an acidifier, an ester of an acidifier, or combinations thereof. Uses of the compositions are also disclosed.

5 Claims, 4 Drawing Sheets

MICROEMULSIONS AND THEIR USE IN METAL WORKING FLUIDS, WOOD STAINS, OR WOOD SEALERS

CROSS-REFERENCE TO RELATED APPLICATIONS

This application is a national stage entry of International Application No. PCT/US15/034488, filed Jun. 5, 2015, which itself claims priority to U.S. Provisional Patent Application No. 62/008,702, filed Jun. 6, 2014, each of the contents of the entirety of which are incorporated by this reference.

TECHNICAL FIELD

The present disclosure relates generally to microemulsions. More particularly, the present disclosure relates to the production and use of microemulsions in solubilizing or dispersing oil.

BACKGROUND

Linseed is the most common oil effectively used to enhance the drying time in paints. Linseed oils are sustainable, last longer and non-toxic with a good environmental profile. Linseed oils are widely used in applications such as concrete, decks, and protection of wood taking advantage of the linseed oil's unique drying properties via slow oxidation on exposure to oxygen and UV light. The drying properties are very similar to solvent based paint and have always been explored to obtain solvent free paint. Drying time is about the same for linseed oil paint as solvent-based based oil paint; however, as linseed oil dries by exposure to oxygen and UV-light, different weather conditions can slightly change the drying times.

Linseed oil is used in solvent and water based paints. In solvent based paints, traditionally straight linseed oil with mineral spirits is used, whereas in the water based pains, the linseed oil in used as an emulsion for easy incorporation. As the linseed oil starts polymerizing in the drying process, the linseed oil protects the water evaporation and leaves a hard film on the surface. This concept has been used for years. However, the linseed oil emulsion is usually available as 50:50 oil/water systems. Such emulsions are not kinetically stable and tend to separate with the environmental condition that limits the shelf life on storage and transportation.

In the paint and coating industries, a universal colorant is one that is designed for use in water borne and solvent borne systems. When universal colorants are added to water borne systems, many changes in the physical properties are encountered in the tint base. The most common effect is the viscosity changes associated with the addition of the colorant, as well as the effect on color development. The main reasons for effects seen with poor color development is due to the improper color compatibility between the colorant and the tint base which results in pigment separation and/or flocculation during the drying of the resultant film. However, typical dispersants used in universal colorants are not biobased and finding a biobased dispersant that is compatible with a universal colorant is a challenge.

In addition to uses in paint, linseed oil is used in concrete applications for a number of benefits. Emulsions of boiled linseed oil have certain physical characteristics suitable for application in concrete as curing and antispalling agents. Curing of wet concrete with the use of a spray technique is believed to retard concrete deterioration and reduce spoiling when the concrete is subjected to winter deicing salts. Emulsions of linseed oil are effective in protecting air entrained concrete from damage that results from the application of deicing materials and concurrent freeze-thaw cycles. The linseed oil emulsions are effective as curing and antispalling agents in concrete.

Other oil emulsions have various uses. For example, methylated seed oil emulsions have many applications such as in oil fields, cleaning, and in the agricultural adjuvant industry. Further, limonene is quite commonly used in cleaning and degreasing applications. If without fine tuning one can make customize product and application by just changing the oil type a great advantages are seen as far as cost savings and transportation are concerned.

However, each of the oil emulsions has drawbacks. For instance, such emulsions are typically made using high energy mixing. The particle is size of the oil droplet in the emulsion is the key towards producing a stable emulsion. Oil and water homogenized at high shear usually results in fine droplet sizes that have a higher surface area and interact better with the added surfactant in stabilizing the emulsion. Keeping such oil and water emulsions stable over time can be a challenge.

Microemulsions are self-assembled systems, form spontaneously with no high energy mixing, and have excellent stability. Further, if a given microemulsion surfactant concentrate can solubilize different types of oils, such microemulsion offers tremendous opportunity towards applications based on the specific oil needs. Thus, needs exist for microemulsions which are able to solubilize such oils.

SUMMARY

In each of its various embodiments, the present invention fulfills these needs and discloses microemulsion concentrates and/or microemulsions that are able to solubilize oils.

In one embodiment, a microemulsion concentrate comprises lecithin, a co-surfactant, and a salt of an acidifier, an ester of an acidifier, or a combination thereof.

In another embodiment, a microemulsion comprises lecithin, a co-surfactant, an oil, and a salt of an acidifier, an ester of an acidifier, or a combination thereof In an additional embodiment, methods of dispersing compounds, such as oils, using the microemulsions and/or microemulsion concentrates are further disclosed.

In a further embodiment, uses of the microemulsion concentrates and/or microemulsions as a cleaning agent, a degreaser, a pigment grinding aid, a wood preservative, a clear coat composition, a wood stain, a metal working fluid, a lubricant, an asphalt remover, an agricultural adjuvant, a bioremediation agent, an oil based lubricant for drilling applications, a water based lubricant for drilling applications, a spacer fluid in well bore applications, or a rig wash in well bore applications are further disclosed.

It should be understood that this disclosure is not limited to the embodiments disclosed in this Summary, and it is intended to cover modifications that are within the spirit and scope of the invention, as defined by the claims.

BRIEF DESCRIPTION OF THE DRAWINGS

The characteristics and advantages of the present disclosure may be better understood by reference to the accompanying figures, in which.

DETAILED DESCRIPTION

Figure 1A:
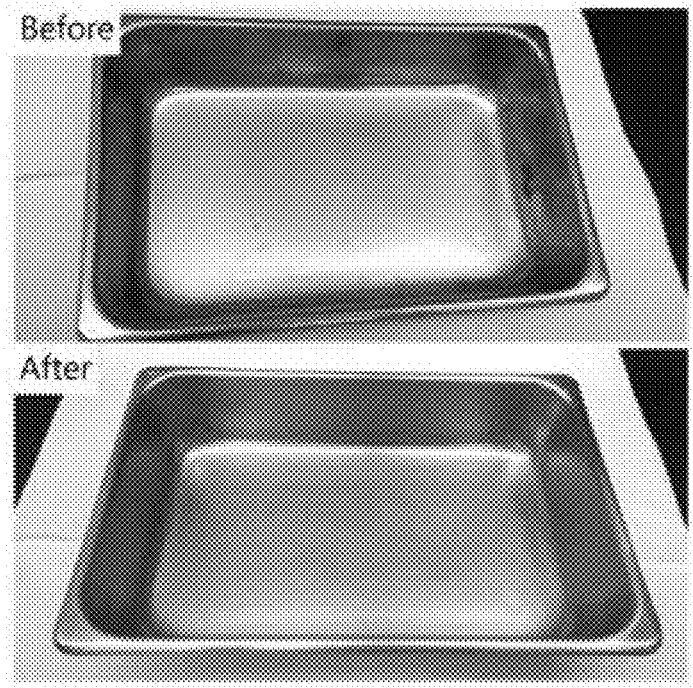
FIG. 1A and FIG. 1B show pictures of cleaning formulations produced with one embodiment of a microemulsion of the present invention.

One benefit of the microemulsions of the present invention is that they are thermodynamically stable one phase systems that are isotropic and form instant stable emulsions once added to water. Such characteristic of the microemulsions of the present invention is that they may be used as a surfactant concentrate that can solubilize different types of oils and provide tremendous opportunities towards applications based on the specific oil needs. Such products offer advantages as far as cost savings and transportation are concerned. This offers a great advantage in shipping the microemulsion in this form where the water is required only at the time of application, not at the time of emulsion formation.

In the present application, including the claims, other than in the operating examples or where otherwise indicated, all numbers expressing quantities or characteristics are to be understood as being modified in all instances by the term "about". Unless indicated to the contrary, any numerical parameters set forth in the following description may vary depending on the desired properties in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, the disclosure set forth herein supersedes any conflicting material incorporated herein by reference.

Lecithin is a lipid substance found in animal and plant tissues such as, for example, egg yolk, soybean, sunflower, and canola or rapeseed. Lecithin includes various constituents including, but not limited to, phospholipids, such as, for example, phosphatidyl choline ("PC"), phosphatidyl inositol ("PI"), and phosphatidyl ethanolamine ("PE"). The amphiphilic property of lecithin makes it an effective processing aid, emulsifier, dispersant and/or surfactant. Lecithin is also a natural ingredient than can form nanodispersions in aqueous mediums and carry high loads of actives. But, in such aqueous mediums, lecithin tends to have limited tolerance to pH and electrolytes.

Lecithin may be used in applications where modification of the boundary layer between substances is desirable. In the presence of immiscible liquid phase, lecithin can reduce the interfacial surface tension and function as an emulsifier. When used with two or more solid phases, lecithin can function as a lubricant and/or release agent.

In a further embodiment, a microemulsion concentrate comprises lecithin, a co-surfactant, and a salt of an acidifier, an ester of an acidifier, or combinations thereof The co-surfactant may have an HLB value of between 10-18. The microemulsion concentrate may also include the salt of the acidifier and the ester of the acidifier. The salt of the acidifier may be sodium lactate and/or the ester of the acidifier may be ethyl lactate.

The lecithin may be selected from the group consisting of crude filtered lecithin, de-oiled lecithin, chemically modified lecithin, enzymatically modified lecithin, standardized lecithin, and combinations of any thereof.

The microemulsion concentrate may have a neutral pH such as between 5-10, 5-10, 6-8, or 6.5-7.5. The microemulsion concentrate may also be essentially free of a free acid such as an organic or mineral acid. Essentially free means less than about 1%, 0.5%, or 0.1% by weight. The microemulsion concentrate may also include fatty acids, a neutralizer, or a combination thereof.

The microemulsion concentrate may consist essentially of the listed elements or even consist of the listed elements.

The acidifier may be selected from the group consisting of lactic acid, propionic acid, methyl acetic acid, acetic acid, fumaric acid, citric acid, ascorbic acid, gluconic acid, gluconic delta lactone acid, adipic acid, malic acid, tartaric acid, a hydroxyl acid, salts of any thereof, esters of any thereof, and combinations of any thereof.

In further embodiments, the microemulsion concentrate may include 35-65% or 45-55% by weight of the lecithin; 7-25% or 10-20% by weight of the co-surfactant; 10-30% or 15-25% by weight of the salt of the acidifier; and/or 5-20% or 8-17% by weight of the ester of the acidifier.

In another embodiment, a microemulsion comprises oil, lecithin, a co-surfactant, and a salt of an acidifier, an ester of an acidifier, or combinations thereof. In an additional embodiment, a microemulsion of the present invention includes any of the microemulsion concentrates of the present invention in combination with an oil or other compound used to create the microemulsion.

The microemulsion may further include a polar solvent, such as one having a dielectric constant in a range of 40-80. The microemulsion may have a pour point of and/or being stable down to a temperature −40° C., and/or may be stable and/or heat resistant at a temperature of up to 200° C. or up to 100° C.

The oil may be selected from the group consisting of linseed oil, soy methyl ester, coconut oil, soybean oil, high oleic oils, mineral oil, limonene, canola oil, sunflower oil, corn oil, tall oil, tung oil, mineral oil, epoxidized vegetable oil, petroleum solvents, alkyds, cedar wood oil, any oil of wide fatty acid profile, and combinations of any thereof.

In yet an additional embodiment, a method of dispersing a compound in a solvent comprises mixing a microemulsion concentrate of the present invention with the compound. The solvent may be non-polar or polar. The method may also include mixing the microemulsion concentrate, the compound, and the polar solvent with a non-polar solvent.

The compound may be an oil, a wax, a universal colorant, a colorant, a dye, or a combination thereof The oil may be selected from the group consisting of linseed oil, soy methyl ester, coconut oil, soybean oil, high oleic oils, mineral oil, limonene, canola oil, sunflower oil, corn oil, tall oil, tung oil, mineral oil, epoxidized vegetable oil, petroleum solvents, alkyds, cedar wood oil, any oil of wide fatty acid profile, and combinations of any thereof.

In yet an additional embodiment, a method of dispersing an oil includes mixing the oil with a microemulsion concentrate of the present invention, thus forming a microemulsion; and dispersing the microemulsion in a solvent. The solvent may be a polar solvent or non-polar solvent. Where the solvent is polar, the method may further include mixing a non-polar solvent with the oil dispersed in the polar solvent.

The oil may be selected from the group consisting of linseed oil, soy methyl ester, coconut oil, soybean oil, high oleic oils, mineral oil, limonene, canola oil, sunflower oil, corn oil, tall oil, tung oil, mineral oil, epoxidized vegetable oil, cedar wood oil, any oil of wide fatty acid profile, and combinations of any thereof.

In the method of dispersing the oil, the oil may be present at 1-70%, 5-65%, 10-60%, 10-50%, or 20-50% by weight and/or the microemulsion may be present at 5-95%, 15-80, or 50-90% by weight.

Uses of the microemulsion concentrate and/or the microemulsions of the present invention as a cleaning agent, a degreaser, a pigment grinding aid, a wood preservative, a concrete coating, a clear coat composition, a wood stain, a metal working fluid, a lubricant, an asphalt remover, an agricultural adjuvant, a bioremediation agent, an oil based lubricant for drilling applications, a water based lubricant for drilling applications, a spacer fluid in well bore applications, or a rig wash in well bore applications are further disclosed.

Also, yet another embodiment of this invention describes a process for producing a microemulsion by mixing lecithin with a surfactant, thus forming a lecithin co-surfactant blend, and mixing a salt of an acidifier, an ester of an acidifier, or combinations thereof with the lecithin co-surfactant, thus forming a microemulsion concentrate.

One aspect of this embodiment describes the use of bio-based and bio-renewal components for preparing such microemulsion concentrates.

In a further embodiment, the microemulsions of the present invention may be used in paints or coatings in combination with a colorant or tint. In one embodiment, the colorant may be a universal colorant, or a colorant that functions in water and non-polar solvent based systems.

Microemulsions are clear, isotropic, thermodynamically stable liquid mixtures including oil, water, and a surfactant. The water phase may contain salt(s) and/or other ingredients. Microemulsions may be prepared from a large number of components. In contrast to ordinary emulsions, microemulsions form upon simple mixing of the components and do not require high shear conditions. In ternary systems, such as micro emulsions, where two immiscible phases (water and 'oil') are present next to the surfactant phase, the surfactant molecules form a monolayer at the interface between oil and water, with the hydrophobic tails of the surfactant molecules dissolved in the oil phase and the hydrophilic head groups in the aqueous phase. Comparable to the binary systems (water/surfactant or oil/surfactant), self-assembled structures of different morphologies can be obtained ranging from (inverted) spherical and cylindrical micelles to lamellar phases and bi-continuous microemulsions. A water-in-oil microemulsion is an optically transparent mixture including oil, water, and surfactant. Water droplets are in a continuous oil phase stabilized by surfactant.

Lecithins suitable for use in the disclosed compositions and methods include, but are not limited to, crude filtered lecithin, fluid lecithin, de-oiled lecithin, chemically and/or enzymatically modified lecithin, standardized lecithin, and blends of any thereof. Lecithins employed in the present disclosure generally tend to have a hydrophilic-lipophilic balance ("HLB") value ranging from 1.0 to 10.0 depending on the processing conditions and additives used to obtain and produce the lecithin product. For example, crude filtered lecithin has an HLB value of approximately 4.0 and favors the formation of water-in-oil emulsions. Standardized lecithin includes co-emulsifiers having HLB values ranging from 10.0 to 24.0, which results in lecithin compositions having HLB values of 7.0 to 12.0 and favoring oil-in-water emulsions. Any lecithin or combinations of lecithins are suitable for use in the disclosed compositions and methods regardless of the initial HLB value of the lecithin. Lecithins useful in the disclosed compositions and methods may comprise co-emulsifiers having a hydrophilic-lipophilic balance value ranging from 10.0 to 24.0, and in certain embodiments 10.0 to 18.0.

The emulsifier and/or surfactant properties of an amphiphilic substance such as lecithin, for example, may be predicted at least in part by the hydrophilic-lipophilic balance ("HLB") value of the substance. The HLB value may function as an index of the relative preference of an amphiphilic substance for oil or water—the higher the HLB value, the more hydrophilic the molecule; the lower the HLB value, the more hydrophobic the molecule. A description of HLB values is provided in U.S. Pat. No., 6,677,327, which is incorporated by reference herein in its entirety. HLB is also described in Griffin, "Classification of Surface-Active Agents by 'HLB,'" *J. Soc. Cosmetic Chemists* 1 (1949); Griffin, "Calculation of HLB Values of Non-Ionic Surfactants," *J. Soc. Cosmetic Chemists* 5 (1954); Davies, "A quantitative kinetic theory of emulsion type, I. Physical chemistry of the emulsifying agent," *Gas/Liquid and Liquid/Liquid Interfaces, Proceedings of the 2d International Congress on Surface Activity* (1957); and Schick, "Nonionic Surfactants: Physical Chemistry", Marcel Dekker, Inc., New York, N.Y., pp. 439-47 (1987), each of which is incorporated by reference herein in its entirety.

Substances of a bio-derived origin are derived from biological materials as opposed to being derived from petrochemical sources. Bio-derived substances may be differentiated from petroleum derived substances by their carbon isotope ratios using ASTM International Radioisotope Standard Method D 6866. As used herein, the term "bio-derived" refers to being derived from or synthesized by a renewable biological feedstock, such as, for example, an agricultural, forestry, plant, fungal, bacterial, or animal feedstock.

Various agencies have established certification requirements for determining bio-derived content. These methods require the measurement of variations in isotopic abundance between bio-derived products and petroleum derived products, for example, by liquid scintillation counting, accelerator mass spectrometry, or high precision isotope ratio mass spectrometry. Isotopic ratios of the isotopes of carbon, such as the $^{13}C/^{12}C$ carbon isotopic ratio or the $^{14}C/^{12}C$ carbon isotopic ratio, can be determined using isotope ratio mass spectrometry with a high degree of precision. Studies have shown that isotopic fractionation due to physiological processes, such as, for example, $CO_2$ transport within plants during photosynthesis, leads to specific isotopic ratios in natural or bio-derived compounds. Petroleum and petroleum derived products have a different $^{13}C/^{12}C$ carbon isotopic ratio due to different chemical processes and isotopic fractionation during the generation of petroleum. In addition, radioactive decay of the unstable $^{14}C$ carbon radioisotope leads to different isotope ratios in bio-derived products compared to petroleum products. Bio-derived content of a product may be verified by ASTM International Radioisotope Standard Method D 6866. ASTM International Radioisotope Standard Method D 6866 determines bio-derived content of a material based on the amount of bio-derived carbon in the material or product as a percent of the weight (mass) of the total organic carbon in the material or product. Bio-derived products will have a carbon isotope ratio characteristic of a biologically derived composition.

Bio-derived materials offer an attractive alternative for industrial manufacturers looking to reduce or replace their reliance on petrochemicals and petroleum derived products. The replacement of petrochemicals and petroleum derived products with products and/or feed stocks derived from biological sources (ie., bio-based products) offer many advantages. For example, products and feed stocks from biological sources are typically a renewable resource. In most instances, bio-derived chemicals and products formed therefrom are less burdensome on the environment than petrochemicals and products formed from petrochemicals. As the supply of easily extracted petrochemicals continues to be depleted, the economics of petrochemical production will likely force the cost of the petrochemicals and petroleum derived products to be higher compared to bio-based products. In addition, companies may benefit from the marketing advantages associated with bio-derived products from renewable resources in the view of a public becoming more concerned with the supply of petrochemicals.

In various embodiments, the disclosed compositions may also comprise one or more co-surfactants. The one or more co-surfactants may comprise one or more anionic surfactants, one or more non-ionic surfactants, or combinations of one or more anionic surfactants and one or more non-ionic surfactants. In various embodiments, the co-surfactant or co-surfactant combinations may have a hydrophilic-lipophilic balance ranging from 10.0 to 24.0, and in some embodiments from 10.0 to 18.0.

Anionic surfactants suitable for use in the disclosed compositions and methods include, but are not limited to, sodium and potassium salts of straight-chain fatty acids, polyoxyethylenated fatty alcohol carboxylates, linear alkyl benzene sulfonates, alpha olefin sulfonates, sulfonated fatty acid methyl ester, arylalkanesulfonates, sulfosuccinate esters, alkyldiphenylether(di)sulfonates, alkylnaphthalenesulfonates, isoethionates, alkylether sulfates, sulfonated oils, fatty acid monoethanolamide sulfates, polyoxyethylene fatty acid monoethanolamide sulfates, aliphatic phosphate esters, nonylphenolphosphate esters, sarcosinates, fluorinated anionics, anionic surfactants derived from oleochemicals, and combinations of any thereof In various embodiments, the surfactant comprises an anionic surfactant, such as, for example, a phosphate ester.

Non-ionic surfactants suitable for use in the disclosed compositions and methods include, but are not limited to, sorbitan monostearate, polyoxyethylene ester of rosin, polyoxyethylene dodecyl mono ether, polyoxyethylene-polyoxypropylene block copolymer, polyoxyethylene monolaurate, polyoxyethylene monohexadecyl ether, polyoxyethylene monooleate, polyoxyethylene mono(cis-9-octadecenyl) ether, polyoxyethylene monostearate, polyoxyethylene monooctadecyl ether, polyoxyethylene dioleate, polyoxyethylene distearate, polyoxyethylene sorbitan monolaurate polyoxyethylene sorbitan monooleate, polyoxyethylene sorbitan monopalmitate, polyoxyethylene sorbitan monostearate, polyoxyethylene sorbitan trioleate, polyoxyethylene sorbitan tristearate, polyglycerol ester of oleic acid, polyoxyethylene sorbitol hexastearate, polyoxyethylene monotetradecyl ether, polyoxyethylene sorbitol hexaoleate, fatty acids, tall-oil, sorbitol hexaesters, ethoxylated castor oil, ethoxylated soybean oil, rapeseed oil ethoxylate, ethoxylated fatty acids, ethoxylated fatty alcohols, ethoxylated polyoxyethylene sorbitol tetraoleate, glycerol and polyethylene glycol mixed esters, alcohols, polyglycerol esters, monoglycerides, sucrose esters, alkyl polyglycosides, polysorbates, fatty alkanolamides, polyglycol ethers, derivatives of any thereof, and combinations of any thereof In various embodiments, the surfactant comprises a non-ionic surfactant, such as, for example, a fatty acid ethoxylate.

In another embodiment, the compositions of the present invention may be food grade and include a food grade surfactant such as, for example, a polysorbate, a polyglycerol ester, a sucrose ester, monoglycerides and/or di glycerides or their counterparts.

The embodiments disclosed herein are also directed to methods or processes of preparing the disclosed compositions. In various embodiments, lecithin is mixed with a cosurfactant at ambient temperature and constantly stirred for a period of time. In another embodiment, a salt of an acidifier, an ester of an acidifier, or combinations thereof is added to the lecithin/co-surfactant blend at ambient temperature and mixed for a period of time, thus forming a microemulsion concentrate.

EXAMPLES

The following exemplary, non-limiting examples are provided to further describe the embodiments presented herein. Those having ordinary skill in the art will appreciate that variations of these Examples are possible within the scope of the invention.

Example 1

This example describes a method of making a lecithin concentrate that is water dispersible. A lecithin-cosurfactant blend was prepared by mixing: fluid lecithin in an amount of 73 percent by weight; a co-surfactant, NINEX MT-610 brand fatty acid ethoxylate (available from Stepan, Northfield, IL) in an amount of 20 percent by weight; and soy fatty acids an amount of 7.0 percent by weight. The components were mixed at 50° C. under constant stirring for between 30 minutes to 60 minutes, thus producing an amber, transparent lecithin concentrate. The lecithin concentrate is hydrophilic and easily dispersible in water, particularly when the HLB is around 10-12. In addition to the fatty acid ethoxylate, other co-surfactants having an HLB of between 10-18 would function as well.

Example 2

69% by weight of the lecithin-cosurfactant blend of Example 1 was mixed with 18% by weight of 60% strength sodium lactate (available from Archer-Daniels-Midland Company, Decatur, Ill.), followed by adding 13% by weight of ethyl lactate (available from Archer-Daniels-Midland Company, Decatur, Ill.) to form this blend. The ingredients were constantly stirred at room temperature for about 30 minutes to obtain a clear system that easily forms a stable milky dispersion in water. The pH of this blend was about 7.0.

Example 3

The microemulsion concentrate of Example 2 at 55% by weight was added to double boiled linseed oil at 45% by weight to form a clear microemulsion that forms a stable dispersion in water. The microemulsion in very hard water tolerant and very heat stable. Heating of the microemulsion to a temperature of 100° C. will not break or darken the microemulsion.

Example 4

The blend from Example 2 is a microemulsion concentrate that is dilutable in soy methyl ester (SME) at any concentration.

| Study No. | Microemulsion Concentrate (Example 2) | Soy methyl ester (SME) | Appearance on water dilution |
|---|---|---|---|
| 1 | 90 | 10 | Milky |
| 2 | 80 | 20 | Milky |
| 3 | 70 | 30 | Milky |
| 4 | 60 | 40 | Milky |
| 5 | 50 | 50 | Milky |

Example 5

The blend from Example 2 is a microemulsion concentrate that is dilutable in linseed oil at any concentration. Linseed oil-Scientific boiled was sourced from Archer Daniels Midland Company, Red Wing, Minn.

| Study No. | Microemulsion Concentrate (Example 2) | Scientific boiled Linseed Oil | Appearance on water dilution |
|---|---|---|---|
| 1 | 90 | 10 | Milky |
| 2 | 80 | 20 | Milky |
| 3 | 70 | 30 | Milky |
| 4 | 60 | 40 | Milky |
| 5 | 50 | 50 | Milky |

Example 6

The blend from Example 2 is a microemulsion concentrate that is dilutable in limonene at any concentration. Lirnonene was sourced from Fischer Scientific.

| Study No. | Microemulsion Concentrate (Example 2) | Limonene | Appearance on water dilution |
|---|---|---|---|
| 1 | 90 | 10 | Milky |
| 2 | 80 | 20 | Milky |
| 3 | 70 | 30 | Milky |
| 4 | 60 | 40 | Milky |
| 5 | 50 | 50 | Milky |

Examples 7-10

The blend from Example 1 is a microemulsion concentrate and can be used to disperse many types of oils in water to form stable milky emulsion.

The product from Example 2 can be used to make a degreaser formulation. The formulations can be made from blends of soy methyl esters (SME) and limonene at different active concentrations. As an example:

| Ingredients in formulation | Example 7 | Example 8 | Example 9 | Example 10 |
|---|---|---|---|---|
| Microemulsion concentrate Ex. 1 | 30 | 30 | 30 | 22 |
| Limonene | 30 | 30 | — | — |
| SME | — | 5 | 30 | 40 |
| Polysorbate 80 | 28 | 28 | 28 | 21 |
| Propylene glycol | 10 | 5 | 10 | 15 |
| Triethanol amine | 2 | 2 | 2 | 2 |

The finished formulation bloom when diluted in water to form a stable milky emulsion at pH=9.

The products from Examples 7, 8, 9, and 10 are dilutable in propylene glycol which results in very low viscosity microemulsions. The product from Example 7 at 60% weight can be diluted with propylene glycol to form a microemulsion that has a pour point as low as −40° F. This microemulsion is also readily water dispersible. A completely biobased composition based on phospholipid chemistry with no flammable components can be made without any addition of volatile organic compounds (VOCs) such as glycol ethers and yet still achieve a low pour point. The products of these Examples could be used a water based lubricants, degreasers, asphalt removers, spacer fluids, stimulation fluids, metal working fluids, oil based and water based lubricants in drilling applications, and as spacer fluids and/or rig wash fluids in well bore applications. The compositions of these Examples are also very heat resistant and can be heated to temperatures as high as about 200° C. without the microemulsion breaking down.

Figure 1B:
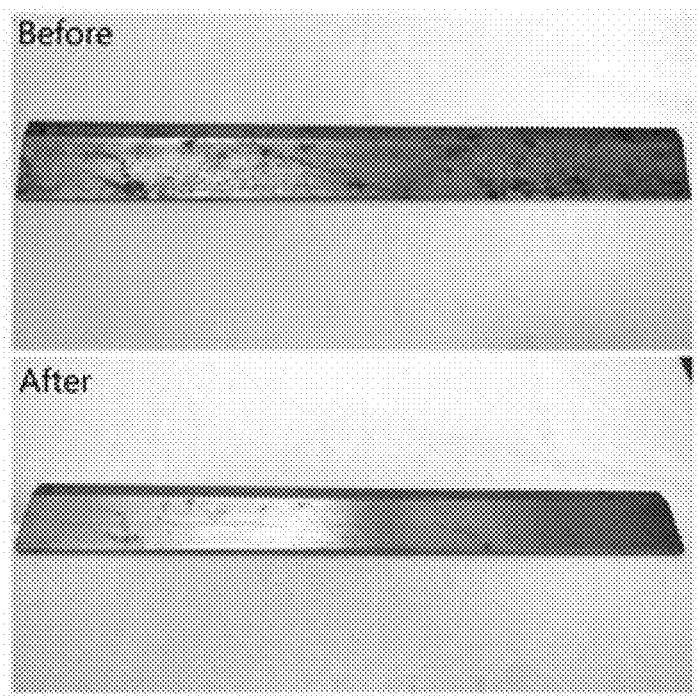

The composition of Example 10 was tested as a degreaser on a stainless steel surface. The microemulsion of Example 10 can be used as is or dispersed in water to form a milky emulsion. As shown in FIG. 1A and FIG. 1B, a surface can be significantly cleaned by spraying the microemulsion on the metal surface and gently scrubbing and rinsing the surface as depicted in the pictures showing surfaces before and after cleaning.

Example 11

The microemulsions of the present invention can also be used to disperse a wide variety of oils with different fatty acid compositions. When it comes to vegetable oils, the microemulsion chemistry can become very complex. The following table shows the fatty acid compositions of various oils:

| Fatty acid compositions of some common oils | | | | |
|---|---|---|---|---|
| | Saturated | 18:1 | 18:2 | 18:3 |
| Linseed | 10 | 16 | 24 | 50 |
| Soybean | 16 | 25 | 51 | 8 |
| Canola | 7 | 66 | 19 | 8 |
| Sunflower | 11 | 20 | 69 | — |
| Tall* | 3 | 46 | 36 | 3 |
| Tung | 5 | 11 | 15 | 69 (conjugated) |

*Tall oil-conjugated diene acids + rosin acids & unsaponifiables account for rest to 100%.

The differences in fatty acid compositions of the various oils contributes to differences in polarity. When making microemulsions, typically the compositions of the components and the amounts thereof have to be tailor made to effectively form a microemulsions. In essence, each microemulsion that has to be made is unique. However, the ability to use a single microemulsion concentrate that, in essence, uses a constant amount of a surfactant and co-surfactant, yet still has the ability to disperse a wide variety of oils having different fatty acid profiles would be beneficiaL This Example shows the ability of the microemulsion of the present invention to effective form microemulsions with a wide array of oils.

Figure 2:
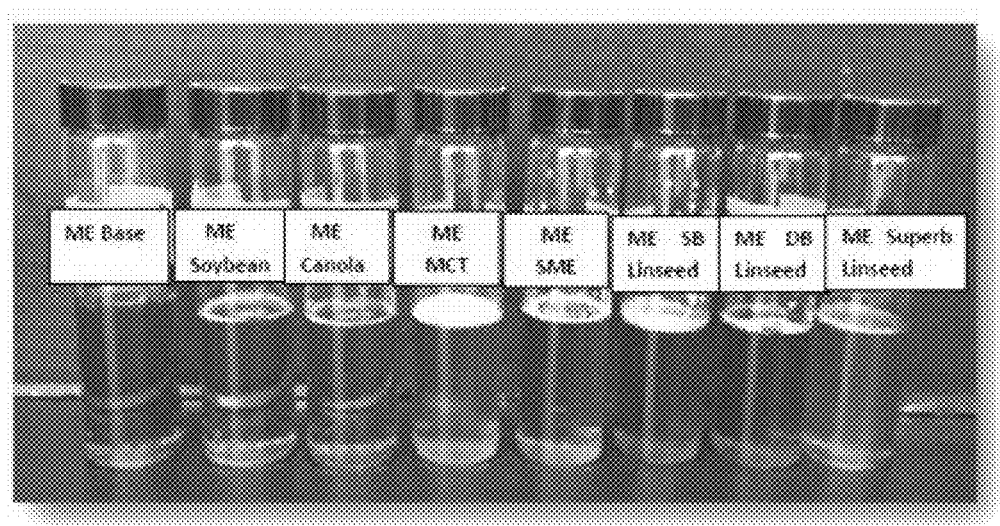
FIG. 2 shows a picture depicting the ability of one embodiment of a microemulsion concentrate of the present invention to form microemulsions with a variety of oils.

To show the ability of the microemulsion concentrates of the present invention having uniform surfactant/co-surfactants and amounts to form microemulsions with oils of varying fatty acids, the microemulsion concentrate of Example was used at 55% and added to 45% by weight of the following oils: soybean oil, canola oil, medium chain triglycerides, soy methyl ester, single boiled linseed oil, double boiled linseed oil, and superb linseed oil. The blends were mixed and a picture of the various blends showing the formed microemulsions are shown in FIG. 2. Other oils that were able to form microemulsions at the same ratios of microemulsion concentrate to oil include tung oil, tall oil, cedar wood oils, and essential oils.

Example 12

Metal working fluid compositions perform a number of useful functions including cooling, lubrication, chip evacuation, and short-term corrosion protection. The metal working fluids show promise in terms of functional requirements (cooling and lubrication) and microfiltration compatibility. Due to environmental concerns, converting to carbide tooling, and increased machine speeds, water diluted metal working fluids are desired. These emulsions and water soluble oils are designed to cool and lubricate. Such water soluble metal working fluids are designed to cool and lubricate which helps reduce abrasive wear of the tool at high temperatures and prevent thermal distortion of the tool caused by residual heat. Soluble metal working fluid concentrates can be diluted with water at different ratios before use and typically contain a surfactant to main the emulsification in the water phase. However, such emulsions suffer from the drawback that they are not very stable and can phase separate. As the microemulsions of the present invention are thermodynamically stable, metal working fluids produced with such microemulsions can provide long term stability that can be readily dispersed in water at the desired time of use.

Vegetable oils can have different oxidative stabilities and when formulating metal working fluids, a vegetable oil with a high temperature stability is desired as many metal working applications involve very high temperatures. Thus, an emulsion stable at such high temperatures is required.

The microemulsion concentrate of Example 1 was used to make a microemulsion based on epoxidized soy methyl ester. The other high stability oils such as high oleic canola, soy, or any methyl esters can also be used in making these metal working fluid formulations. The formulation of the 2 compositions produced are shown in the following table.

| Ingredients in formulation | Formulation 1 | Formulation 2 |
|---|---|---|
| Microemulsion of Ex. 1 | 30 | 30 |
| Epoxidized soy methyl ester | 30 | 25 |
| Soy methyl ester | — | 5 |
| Polysorbate 80 | 28 | 28 |
| Propylene glycol | 10 | 10 |
| Triethanol amine | 2 | 2 |

These microemulsions form stable milky emulsions in water, and the neat microemulsion is very high temperature stable and has excellent freeze thaw properties, with a low pour point.

Example 13

Wood stain products are designed to protect wood surfaces and give a decorative finish. The stains are available in different color shades and can accentuate the natural finish and texture of wood. Generally, the wood stains are suspensions with added colorants and may be available as oil or water based, depending on the solvent used. In wiping stains compositions, natural oils have been used in penetrating stains since they cure by air absorption and to strengthen the finish. Linseed and tung oils are commonly used as drying oils in stains. Such stains are usually applied with a brush or rag, and the stain is wiped off to control the depth of the stain. Unlike paints that form a surface on the applied substrate, the stains soak into the wood and accent the wood grain instead of hiding the grain. The stains help prevent the wood from cracking, peeling, chipping or blistering that can be encountered with pains. The tinted wiping stain formulations of this Example are based on double boiled linseed oil using waterbased colorants (i.e., Timbasol) and universal colorants (ie., the 888 series).

The microemulsion concentrate of Example 2 is mixed at 55% with 45% by weight of double boiled linseed oil to produce a linseed oil microemulsion, and placed into a wood stain formulation as follows. 24.2% of the double boiled linseed oil microemulsion is slowly mixed with 72.7% water. The dispersed double boiled linseed oil in water is tinted with 1.2% of the colorant, Timbasol WA transparent YO PW-601, 0.6% of the colorant, Timbasol WA transparent RO PW-602, 0.7% of the colorant 888-1810 yellow oxide, 0.3% of the colorant 888-1045 red oxide, 0.2% of the colorant 888-9907 black, and the biocide, Aciticide RS, for a total of 100%. The formulation has the following characteristics: 25.54% non-volatiles; 8.37 lbs/gal; viscosity of 60 clear, KU; a ford cup 4 value (clear) of 19 seconds; a tinted viscosity of 57 KU; a ford cup 4 value (tinted) of 18 seconds, and pH of between 7-8.

Figure 3:
FIG. 3 shows pictures of the ability of one embodiment of a microemulsion of the present invention to produce a wood stain.

The waterborne penetrating oil stain of this Example had a good color acceptance in both universal and waterbased colorants. No additional surfactants/dispersants were needed. The VOC content was low for a water based stain formulation. As shown in FIG. 3, the formulation has good drying properties (1-2 hours of drying) which resulted in a uniform flat finish. The wood stain of this Example showed none to very minimal wood grain raising. The finished formulation was also stable on heat ageing for 2 weeks at 120° F. The wood stain of this Example also had an easy clean up with just soap and water.

Example 14

A clear coat or wood sealer composition was prepared using the microemulsions of the present invention. The microemulsion concentrate from Example 2 was used at 55% by weight and added to 45% by weight of double boiled linseed oil. The produced double boiled linseed oil microemulsions were dispersed in water and used to produce a clear coat composition including: 37% by weight of the double boiled linseed oil microemulsion; 61.7% water; 0.2% defoamer (BYK 093); 0.1% biocide (Proxel GXL); and 1.0% biocide (Polyphase P-20T). The resulting clear coat composition has a viscosity, Zahn Cup #2 of 31.6 seconds and a pH of 6-7.

Figure 4:
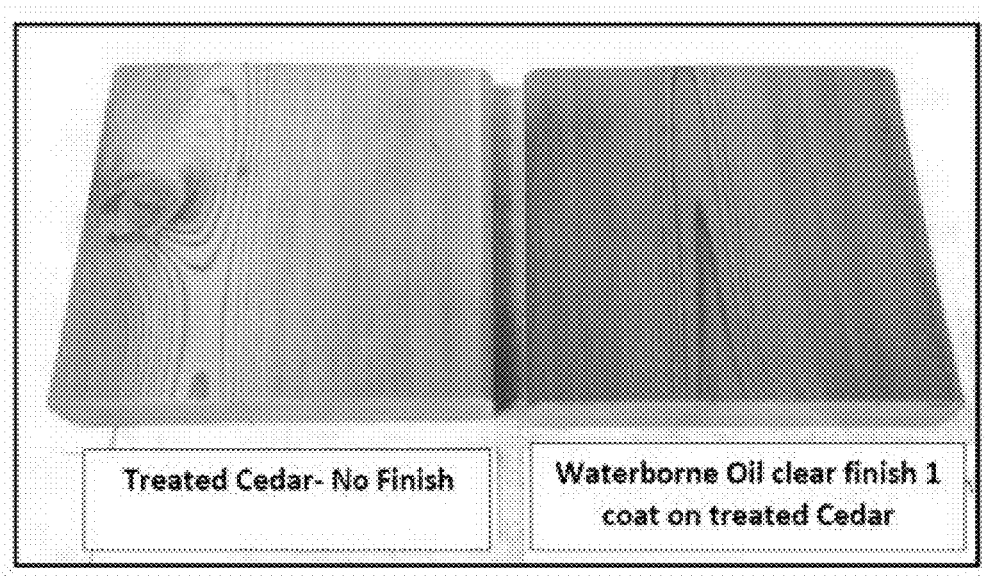
FIG. 4 shows pictures of the ability of one embodiment of a microemulsion of the present invention to produce a clear coating.

The clear coat composition of this Example had excellent wetting and penetration of wood, in addition to an enhanced natural appearance of the wood as compared to clear coat compositions based on pure alkyd emulsions or acrylic/alkyd hybrid emulsions. The microemulsion based clear coat composition of this Example may also be blended with acrylic/alkyd hybrid polymers to improve wetting/penetration and the natural appearance of wood. The clear coat composition of this Example is low VOC and as shown in FIG. 4, dries to a uniform flat finish in about 1-2 hours. The clean coat composition showed none to minimal wood grain raising. The clear coat composition of this Example is also stable for 2weeks on heat ageing, and has easy clean up in soap and water.

Example 15

The microemulsions of the present invention may also be used in making wood stains/sealers with a built in pigment system. Such systems may be easily diluted by an end customer in water and would be ready to use. Such systems would also prevent shipping all of the water in an emulsion.

In this Example, a pigment dispersion was made using the microemulsion concentrate of Example 2. The following ingredients were added one at a time under moderate mixing speed and mixing continued until homogenous: 57.9% by weight of the microemulsion concentrate of Example 2; 0.3% by weight of Byk 028 (dispersed in a media mill to 6-7 Hegman grind); 37.6% by weight of red iron oxide; 3.9% by weight of water; 0.3% by weight Byk 028; and 0.1% by weight Kathon LK (1.5%). The pigment dispersion had the following properties: a FOG (Hegman) of 6.5-7; a pH of 6.98; and a viscosity of 86.2 KU.

The red iron oxide pigment dispersion can be readily diluted in water to obtain a tinted concrete stain/sealer system. Such formulations avoid the shipping cost of the water normally used to make water based sealers. Further, the microemulsion technology of the present invention is very tolerant to high electrolyte content and, thus, the variability in water source should not be a concern for an end customer. The red iron oxide microemulsion concentration can also be diluted in a non-polar solvent and allows the use of the microemulsion concentrates/microemulsions of the present invention in universal colorant formulations.

Example 16

Waxes could also be added to the microemulsions of the present invention at various concentrations to produce a hydrophobic effect to a finished stain or sealer formulation. The presence of the wax may provide some water resistance on exterior surfaces such as decks, posts, railings, doors, and/or windows. Beeswax at 10% weight was added to 90% of a soy oil microemulsion made substantially as those described in Example 4. The beeswax was heated until the beeswax completely melted. On cooling, the microemulsion was viscous, but water dispersible.

Example 17

Water or oil soluble wood preservatives can also be added to the microemulsions of the present invention. When applied as a neat composition or in an emulsion, the wood preservatives in combination with the microemulsions of the present invention may create protection for the wood from termites or other wood degrading agent.

Cedar wood oil is a good fungicide and has a good effect on mildew on wood. Microemulsions can be made with up to 30% by weight of cedar wood oil substantially as described in Example 6.

This disclosure has been described with reference to certain exemplary embodiments, compositions, and uses thereof However, it will be recognized by those of ordinary skill in the art that various substitutions, modifications, or combinations of any of the exemplary embodiments may be made without departing from the spirit and scope of the disclosure. Thus, the disclosure is not limited by the description of the exemplary embodiments, but rather by the appended claims as originally filed.

What is claimed is:

1. A method of dispersing an oil in a metal working fluid comprising:
   mixing 10-50% by weight of an oil selected from the group consisting of a methyl ester, a high oleic canola oil, an epoxidized vegetable oil, and combinations of any thereof, with 50-90% by weight of a microemulsion concentrate comprising:
   a) lecithin;
   b) a co-surfactant;
   c) a salt of an acidifier, and
   d) an ester of an acidifier, thus forming a microemulsion; and
   dispersing the microemulsion in a polar solvent and a non-ionic surfactant different from the surfactant of the microemulsion.

2. The method according to claim 1, further comprising mixing the polar solvent and the microemulsion with a non-polar solvent.

3. A method of adding an oil to a wood stain or wood sealer, the method comprising:
   A) mixing the oil with a microemulsion concentrate comprising:
   a) lecithin;
   b) co-surfactant;
   c) a salt of an acidifier, and
   d) an ester of an acidifier, thus forming a microemulsion; and
   B) mixing the oil and microemulsion with an oil stain or a wood sealer, wherein the oil stain comprises water, a biocide, a defoamer, and a water-soluble or oil-soluble wood preservative, and the wood sealer comprises water, a biocide, a defoamer, a wax, and a water-soluble or oil-soluble wood preservative.

4. The method of claim 3, wherein the co-surfactant is selected from the group consisting of fatty acid ethoxylate, fatty acids, and the combination thereof.

5. The method of claim 3, wherein the oil is selected from the group consisting of linseed oil, soy methyl ester, coconut oil, soybean oil, high oleic oils, mineral oil, limonene, canola oil, sunflower oil, corn oil, tall oil, tung oil, mineral oil, epoxidized vegetable oil, petroleum solvents, alkyds, cedar wood oil, any oil of wide fatty acid profile, and combinations of any thereof.

* * * * *